United States Patent
Kim et al.

(10) Patent No.: US 12,340,508 B2
(45) Date of Patent: Jun. 24, 2025

(54) METHOD AND SYSTEM FOR AUTOMATICALLY MANAGING CLINICAL TRIAL IMAGE EVALUATION DATA

(71) Applicant: TRIAL INFORMATICS INC., Seoul (KR)

(72) Inventors: Kyung Won Kim, Seoul (KR); Young Bin Shin, Seoul (KR); Ji Woo Lee, Seongnam-si (KR); Jung Hyun Lee, Seoul (KR)

(73) Assignee: TRIAL INFORMATICS INC., Seoul (KR)

( * ) Notice: Subject to any disclaimer, the term of this patent is extended or adjusted under 35 U.S.C. 154(b) by 357 days.

(21) Appl. No.: 17/932,936

(22) Filed: Sep. 16, 2022

(65) Prior Publication Data
US 2023/0017940 A1 Jan. 19, 2023

Related U.S. Application Data

(63) Continuation of application No. PCT/KR2021/003157, filed on Mar. 15, 2021.

(30) Foreign Application Priority Data

Mar. 18, 2020 (KR) .................. 10-2020-0033166

(51) Int. Cl.
*G16H 10/20* (2018.01)
*G06T 7/00* (2017.01)
(Continued)

(52) U.S. Cl.
CPC .............. *G06T 7/0012* (2013.01); *G06T 7/62* (2017.01); *G16H 30/40* (2018.01); *G06T 2207/30004* (2013.01)

(58) Field of Classification Search
USPC .................. 128/897–899, 920, 922–925; 600/300–585, 1–243; 606/1–236,
(Continued)

(56) References Cited

U.S. PATENT DOCUMENTS

| | | | |
|---|---|---|---|
| 2016/0246788 A1* | 8/2016 | Thangaraj | G16H 80/00 |
| 2019/0057137 A1* | 2/2019 | Bradham | G16H 10/20 |
| 2020/0219593 A1* | 7/2020 | Eteminan | G06F 8/73 |

FOREIGN PATENT DOCUMENTS

| | | | |
|---|---|---|---|
| JP | 2009-075951 A | 4/2009 | |
| JP | 2017-501494 A | 1/2017 | |

(Continued)

OTHER PUBLICATIONS

Keiichi Yamamoto et al., "A pragmatic method for transforming clinical research data from the research electronic data capture "REDCap" to Clinical Data Interchange Standards Consortium (CDISC) Study Data Tabulation Model (SDTM): Development and evaluation of REDCap2SDTM", Journal of Biomedical Informatics, May 6, 2017, vol. 70, pp. 65-76.

(Continued)

*Primary Examiner* — Marcellus J Augustin
(74) *Attorney, Agent, or Firm* — Studebaker Brackett PLLC

(57) ABSTRACT

Provided are a method and system for automatically managing clinical trial image evaluation data. The method automatically managing clinical trial image evaluation data comprises the operations of: obtaining first image evaluation data and second image evaluation data from a first evaluator and a second evaluator, respectively; analyzing the obtained image evaluation data by evaluation items, whether the obtained image evaluation data conforms to preset evaluation rules; in a case in which the obtained image evaluation data includes an evaluation item which does not conform to the evaluation rules, automatically providing a query includ- (Continued)

ing a correction request and help with respect to the evaluation item that does not conform to the evaluation rules; and determining whether the first image evaluation data and the second image evaluation data match each other with respect to the evaluation items.

10 Claims, 11 Drawing Sheets

(51) Int. Cl.
*G06T 7/62* (2017.01)
*G16H 30/20* (2018.01)
*G16H 30/40* (2018.01)
*G16H 50/20* (2018.01)

(58) Field of Classification Search
USPC .................................................. 606/900–916
See application file for complete search history.

(56) References Cited

FOREIGN PATENT DOCUMENTS

| | | |
|---|---|---|
| KR | 10-1226056 B1 | 1/2013 |
| KR | 10-1766473 B1 | 8/2017 |
| KR | 10-2019-0046911 A | 5/2019 |
| WO | 2012/046842 A1 | 4/2012 |

OTHER PUBLICATIONS

Office Action issued in KR 10-2020-0033166; mailed by the Korean Intellectual Property Office on Aug. 26, 2021; with English language translation.

International Search Report issued in PCT/KR2021/003157; mailed Jun. 21, 2021.

\* cited by examiner

| # | Organ | Site | Series# | Image# | Method | Method (Other) | Measurement (mm) |
|---|---|---|---|---|---|---|---|
| 1 | Lymphnode | input ✗ | 14 ✓ | 25 ✓ | Other | input ✗ | input ✗ |
| 2 | Lung | LUL ✓ | 16 ✓ | input ✗ | PET/CT | input | 5 |

FIG. 9

| Evaluator<br>Evaluation Date | 1st evaluator<br>08.09.2019 | 2nd evaluator<br>08.09.2019 | 3rd evaluator<br>08.09.2019 |
|---|---|---|---|
| TR1 Lung / LUL / CT | 55mm (S:355) | 54mm (S:355) | 64.2mm (S:355) |
| TR2 Lung / LUL1 / MR | 55.4mm (S:453) | 53.1mm (S:453) | 63.2mm (S:453) |
| TR3 Liver / LUL2 / CT | 55.54mm (S:554) | 51.4mm (S:554) | 68.54mm (S:554) |
| Sum Measurement | xxx.xx | xxx.xx | xxx.xx |
| BL | xxx.xx | xxx.xx | xxx.xx |
| Nadir | xxx.xx | xxx.xx | xxx.xx |
| %change_BL | xxx.xx% | xxx.xx% | xxx.xx% |
| %change_Nadir | xxx.xx% | xxx.xx% | xxx.xx% |
| Response (RECIST 1.1) | SD | SD | PD |
| Response (iRECIST 1.1) | iSD | iSD | iUPD |

Do not disacord the response (iRECIST) value. Select the reading result.

FIG. 10

| Row | STUDYID | DOMAIN | USUBJID | MISEQ | MIGRPID | MITESTCD | MITEST | MISTDTL | MIORRES | MIORRESU | MISTRESN | MISTRESU | MISPEC | MILOC | MIMETHOD | MIDY | VISIT |
|---|---|---|---|---|---|---|---|---|---|---|---|---|---|---|---|---|
| 1 | ABC | MI | ABC-1001 | 1 | 1 | TTF1 | Thyroid Transcription Factor 1 | The percentage of cells with 0 intensity of staining | 25 | % | 25 | % | TISSUE | LUNG | IHC | | SCREENING |
| 2 | ABC | MI | ABC-1001 | 2 | 1 | TTF1 | Thyroid Transcription Factor 1 | The percentage of cells with 1+ intensity of staining | 40 | % | 40 | % | TISSUE | LUNG | IHC | | SCREENING |
| 3 | ABC | MI | ABC-1001 | 3 | 1 | TTF1 | Thyroid Transcription Factor 1 | The percentage of cells with 2+ intensity of staining | 35 | % | 35 | % | TISSUE | LUNG | IHC | | SCREENING |
| 4 | ABC | MI | ABC-1001 | 4 | 1 | TTF1 | Thyroid Transcription Factor 1 | The percentage of cells with 3+ intensity of staining | 0 | % | 0 | % | TISSUE | LUNG | IHC | | SCREENING |
| 5 | ABC | MI | ABC-1001 | 5 | 1 | TTF1 | Thyroid Transcription Factor 1 | H-Score of staining | 110 | | 110 | | TISSUE | LUNG | IHC | Y | SCREENING |

METHOD AND SYSTEM FOR AUTOMATICALLY MANAGING CLINICAL TRIAL IMAGE EVALUATION DATA

CROSS-REFERENCE TO RELATED APPLICATION

The present application is a continuation of International Patent Application No. PCT/KR2021/003157, filed on Mar. 15, 2021, which is based upon and claims the benefit of priority to Korean Patent Application No. 10-2020-0033166 filed on Mar. 18, 2020. The disclosures of the above-listed applications are hereby incorporated by reference herein in their entirety.

BACKGROUND

1. Technical Field

The present disclosure relates to a method and a system for automatically managing clinical trial image evaluation data.

2. Description of Related Art

A clinical trial is a test or a research process conducted on humans to prove the efficacy and safety of a new drug or medical device for approval, prior to development and marketing. Recently, as the market size and importance of clinical trials have grown steadily in recent years, the importance of ensuring the quality of evaluation data in clinical trials has increased. This is because, in the end, whether the results of a clinical trial can be trusted, for example, whether there were any problems in the clinical trial, whether there were any violations of the clinical trial protocol or regulations, SOP, etc. is ultimately determined based on the evaluation data.

In particular, recently, as we enter the era of immuno-oncology drugs and artificial intelligence (AI) medical devices, clinical trial image evaluation criteria and evaluation procedures are becoming very complicated. Because many image evaluators generate image evaluation data by reading images according to complex evaluation criteria and evaluation procedures, management of image evaluation data is a heavy burden.

For instance, currently, data managers manually verify the RECIST/iRECIST results noted by the evaluators, arrange errors and corrections, and pass queries to the evaluators. The evaluators review the queries, and return to the evaluation stage to make corrections. Repeating the above-mentioned process manually consumes a lot of time and manpower.

In addition, conventionally, each of the plurality of procedures for evaluating clinical trial images is performed through a separate program and system, and so, it is difficult to efficiently manage clinical trial-related data.

SUMMARY

The present disclosure has been made to solve the above-mentioned problems occurring in the prior art, and in an aspect of the present disclosure, an object of the present disclosure is to provide a method and a system for automatically managing clinical trial image evaluation data capable of automatically performing complex procedures for evaluating clinical trial images, not manually.

Moreover, another object of the present disclosure is to provide a method and a system for automatically managing clinical trial image evaluation data capable of minimizing errors in the process of evaluating the clinical trial images, and inputting image evaluation data meeting the evaluation criteria and evaluation procedure.

In addition, a further object of the present disclosure is to provide a method and a system for automatically managing clinical trial image evaluation data capable of integrating and comprehensively managing a plurality of procedures for evaluating clinical trial images.

The aspects of the present disclosure are not limited to those mentioned above, and other aspects not mentioned herein will be clearly understood by those skilled in the art from the following description.

To accomplish the above-mentioned objects, according to an aspect of the present disclosure, there is provided a method for automatically managing clinical trial image evaluation data, generated when a clinical trial image is evaluated, the method performed by a computer and comprising the operations of: obtaining first image evaluation data and second image evaluation data from a first evaluator and a second evaluator, respectively; analyzing the obtained image evaluation data by evaluation items, whether the obtained image evaluation data conforms to preset evaluation rules; in a case in which the obtained image evaluation data includes an evaluation item which does not conform to the evaluation rules, automatically providing a query including a correction request and help with respect to the evaluation item that does not conform to the evaluation rules; and determining whether the first image evaluation data and the second image evaluation data match each other with respect to the evaluation items.

Moreover, the image evaluation data includes a numerical analysis value for a target object, the numerical analysis value is calculated based on reference data included in the evaluation rules, and the reference data includes measurement standard for types of target objects.

Furthermore, the obtaining operation includes the operations of: setting a region of interest; and automatically measuring and providing a numerical analysis value for reference with respect to the target object in the region of interest.

In this instance, the numerical analysis value is at least one among the number, length, area, volume, etc. of the target objects. In addition, the numerical analysis value is calculated based on the maximum diameter of the target object.

Moreover, in the determining operation, an evaluation item mismatched between the first image evaluation data and the second image evaluation data is provided.

Furthermore, the method further includes the operations of: obtaining the final image evaluation data; and converting the final image evaluation data into a standard format, wherein the final image evaluation data is image evaluation data generated in a case in which a moderator performs adjustment based on the image evaluation data input from the plurality of evaluators. Additionally, the standard format is a study data tabulation model (SDTM) format of clinical data interchange standards consortium (CIDSC).

According to an aspect of the present disclosure, there is provided a system for automatically managing clinical trial image evaluation data generated when a clinical trial image is evaluated, including: an image evaluation data obtaining unit which obtains first image evaluation data and second image evaluation data from a first evaluator and a second evaluator, respectively; an image evaluation data error determining unit analyzing the obtained image evaluation data by evaluation items, whether the obtained image evaluation data conforms to preset evaluation rules; a query providing unit automatically providing a query including a correction request and help with respect to an evaluation item that does not conform to the evaluation rules in a case in which the obtained image evaluation data includes the evaluation item which does not conform to the evaluation rules; and an image evaluation data comparing and analyzing unit which checks whether the first image evaluation data and the second image evaluation data match each other with respect to the evaluation items.

BRIEF DESCRIPTION OF THE DRAWINGS

FIG. 5 is an exemplary diagram of a UI provided to an evaluator based on reference data according to an embodiment of the present disclosure.

FIG. 7 is an exemplary diagram illustrating a query provided to the evaluator in the process of obtaining image evaluation data according to an embodiment of the present disclosure.

FIG. 9 is an exemplary diagram illustrating a state in which a mismatch evaluation item is provided according to an embodiment of the present disclosure.

FIG. 10 is an exemplary diagram illustrating a state in which the image evaluation data is converted into SDTM format of CDISC according to an embodiment of the present disclosure.

DETAILED DESCRIPTION

Figure 1:
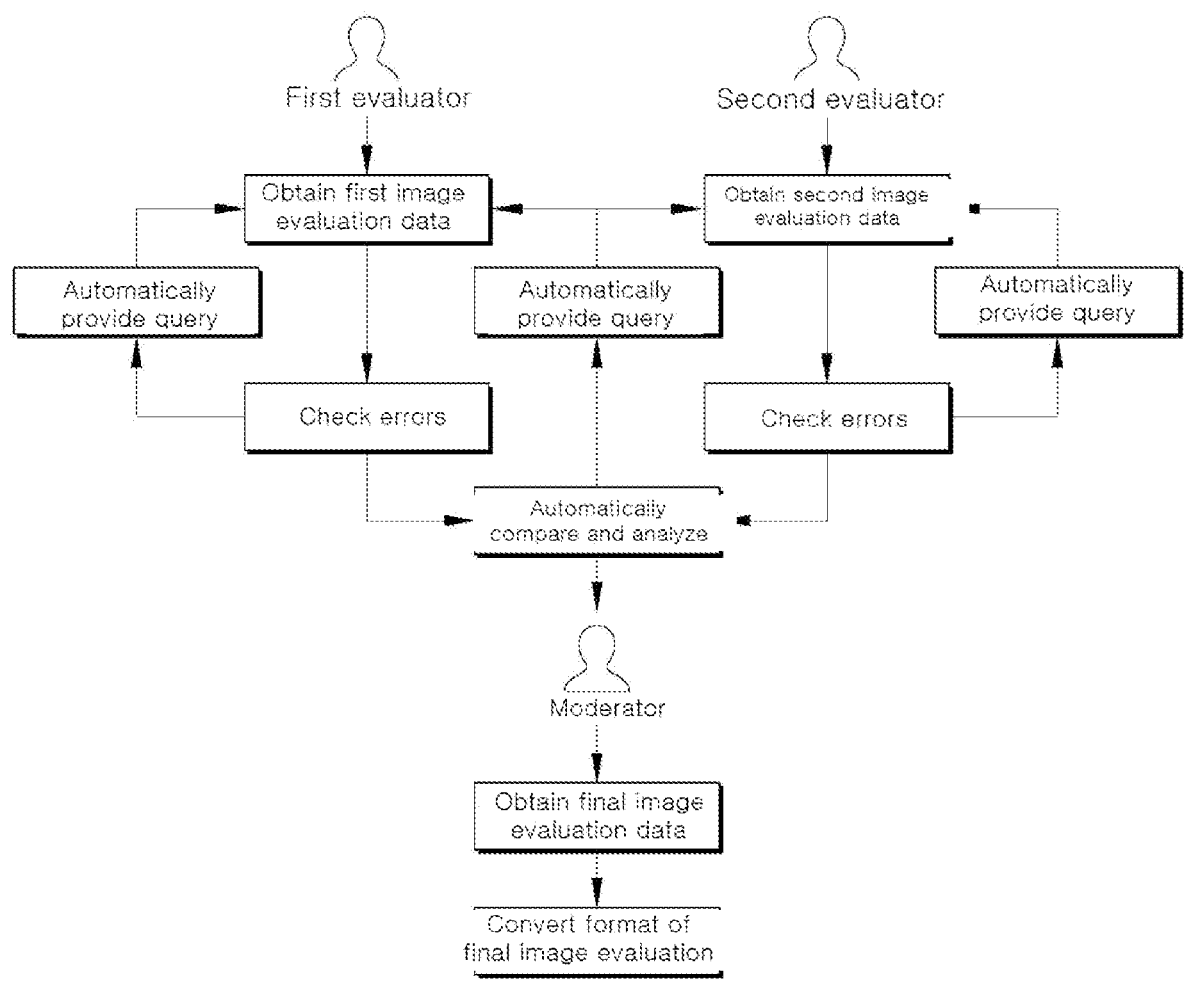
FIG. 1 is a conceptual diagram schematically illustrating a process of managing image evaluation data in a system for automatically managing clinical trial image evaluation data according to an embodiment of the present disclosure.

Advantages and features of the present disclosure and methods accomplishing the advantages and features will become apparent from the following detailed description of exemplary embodiments with reference to the accompanying drawings. However, the present disclosure is not limited to exemplary embodiment disclosed herein but will be implemented in various forms. The exemplary embodiments are provided so that the present disclosure is completely disclosed, and a person of ordinary skilled in the art can fully understand the scope of the present disclosure. Therefore, the present disclosure will be defined only by the scope of the appended claims.

Terms used in the specification are used to describe specific embodiments of the present disclosure and are not intended to limit the scope of the present disclosure. In the specification, the terms of a singular form may include plural forms unless otherwise specified. It should be also understood that terms such as 'include' or 'have' in the specification are used to mean that there is no intent to exclude existence or addition of other components besides components described in the specification. In the detailed description, the same reference numbers of the drawings refer to the same or equivalent parts of the present disclosure, and the term "and/or" is understood to include a combination of one or more of components described above. It will be understood that terms, such as "first" or "second" may be used in the specification to describe various components but are not restricted to the above terms. The terms may be used to discriminate one component from another component. Therefore, of course, the first component may be named as the second component within the scope of the present disclosure.

Unless otherwise defined, all terms (including technical and scientific terms) used herein have the same meaning as commonly understood by those skilled in the technical field to which the present disclosure pertains. It will be further understood that terms, such as those defined in commonly used dictionaries, should not be interpreted in an idealized or overly formal sense unless expressly so defined herein.

In this specification, "image evaluation data" means data generated as an evaluator performs image evaluation (reading) of a clinical trial.

In this specification, "final image evaluation data" refers to image evaluation data generated as a moderator performs adjustment based on the image evaluation data obtained from a plurality of evaluators. That is, the final image evaluation data refers to image evaluation data generated by final determination by adjusting and determining mismatch items based on a plurality of obtained image evaluation data.

In this specification, "target object" means an object to be evaluated in a clinical trial image. For example, the target object may be a specific tissue, organ, lesion, tumor, lymphoma, cell, cancer cell, thrombus, etc., but is not limited thereto.

In this specification, "numerical analysis value" means a value quantified with respect to the characteristics of a target object. For example, the numerical analysis value may be the number, length, area, volume, etc. of the target objects, but is not limited thereto.

Hereinafter, preferred embodiments of the present disclosure will be described in detail with reference to the accompanying drawings.

FIG. 1 is a conceptual diagram schematically illustrating a process of managing image evaluation data in a system for automatically managing clinical trial image evaluation data according to an embodiment of the present disclosure.

Referring to FIG. 1, the system 100 for automatically managing clinical trial image evaluation data according to an embodiment of the present disclosure is a system which obtains image evaluation data from a plurality of evaluators (clinical trial image evaluators), compares and analyzes the image evaluation data, provides the same to the moderator, and obtains the final image evaluation data from the moderator to automatically convert the data into a standard format.

Furthermore, the system 100 for automatically managing clinical trial image evaluation data according to an embodiment of the present disclosure can automatically provide a query by determining errors in the image evaluation data obtained in the process of obtaining image evaluation data, or automatically provide a query based on a result of comparative analysis of a plurality of pieces of image evaluation data.

Hereinafter, the system 100 for automatically managing clinical trial image evaluation data will be described in detail with reference to FIGS. 2 to 10.

Figure 2:
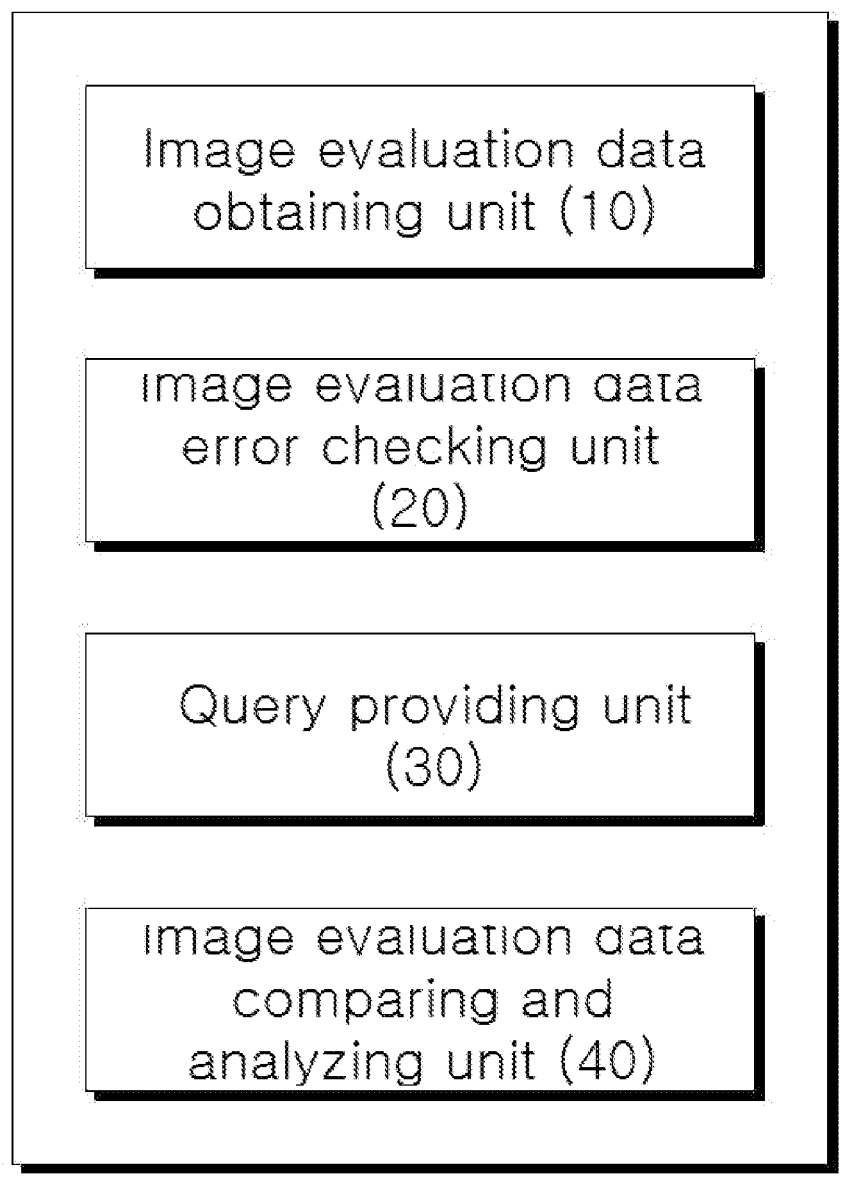
FIG. 2 is a diagram illustrating the system for automatically managing clinical trial image evaluation data according to an embodiment of the present disclosure.

FIG. 2 is a diagram illustrating the system 100 for automatically managing clinical trial image evaluation data according to an embodiment of the present disclosure.

Referring to FIG. 2, the system 100 for automatically managing clinical trial image evaluation data according to an embodiment of the present disclosure includes an image evaluation data obtaining unit 10, an image evaluation data error determining unit 20, and a query providing unit 30, and an image evaluation data comparing and analyzing unit 40.

In an embodiment, the system 100 for automatically managing clinical trial image evaluation data is a two-layered system composed of a server system and a client system to efficiently meet regulations and requirements. In this instance, the server system performs roles, such as system security, data archive, backup and audit trail, and the client system performs de-identification, image transmission, image viewer, image quality control, electronic record management, etc.

The image evaluation data obtaining unit 10 serves to obtain image evaluation data from one or more evaluators or to obtain final image evaluation data from a moderator.

In an embodiment, the plurality of evaluators independently perform evaluation on the same clinical trial image to generate respective image evaluation data. In addition, the moderator adjusts the final evaluation based on the plurality of pieces of image evaluation data obtained from the plurality of evaluators to generate the final image evaluation data. As described above, since the plurality of evaluators perform evaluation on the same clinical trial image, more accurate and high-quality final image evaluation data can be generated.

As a specific example, the image evaluation data obtaining unit 10 obtains first image evaluation data and second image evaluation data from a first evaluator and a second evaluator, respectively. In this instance, the first image evaluation data and the second image evaluation data are image evaluation data generated when the first evaluator and the second evaluator respectively evaluate the same clinical trial image. The moderator obtains the first image evaluation data and the second image evaluation data, adjusts mismatch items between the first and second image evaluation data, and makes a final decision to generate the final image evaluation data. Details of the process of generating the final image evaluation data will be described later.

In another embodiment, the evaluator may obtain clinical trial images from a plurality of institutions. That is, the evaluator may receive not only the clinical trial image generated by the institution to which the evaluator belongs, but also a clinical trial image generated by another institution, and generate image evaluation data by performing evaluation on the received clinical trial image. Thereby, institutions that lack material or human resources to evaluate clinical trial images can participate in clinical trials, and obtain image evaluation data with guaranteed quality that complies with domestic and foreign regulations.

The image evaluation data error determining unit 20 analyzes whether the image evaluation data obtained by the image evaluation data obtaining unit 10 conforms to preset evaluation rules for each evaluation item.

"Evaluation rules" are evaluation guidelines that are stored and set in the system in advance. For example, the evaluation rules may include rules for evaluation items that the evaluator must input when performing evaluation, evaluation items that must be input with a value of a specific range, evaluation items that must be measured by a specific measurement method, etc., but the present disclosure is not limited thereto.

That is, the image evaluation data error determining unit 20 analyzes in real-time whether there are evaluation items against the evaluation rules, for instance, whether the image evaluation data that are being input or have been input based on the evaluation rules have missing evaluation items, whether there are evaluation items exceeding the input range, or whether there is an incorrect measurement method.

The query providing unit 30 automatically generates and provides a query for evaluation items in which the obtained image evaluation data does not conform to the evaluation rules as a result of the analysis of the image evaluation data error determining unit 20.

Here, "query" is to make an inquiry to induce a user to input image evaluation data to conform to the evaluation rules.

In an embodiment, the query includes a system error query and a clinical trial error query. The system error query is a query for technical problems such as image upload, and a clinical trial error query is a query for data omissions, an excess of the range, incorrect measurement method application, and the like. As a specific example, the query is provided to distinguish whether it is a system error query or a clinical trial error query, so that the user can immediately determine the cause of the error.

In another embodiment, the query providing unit 30 may use a query language, a structured query language (SQL), etc. to provide a query, and may be prepared and provided in a form that is easy for evaluators and coordinators to recognize. That is, the generated query can be automatically converted and provided in a form that even a user who does not know the programming language can understand. In addition, the query may include an amendment request, help, a description of the query content, and the like.

For example, in a case in which the evaluator omits a specific evaluation item, a query may be provided in the form of 'Missing data', and a message 'RECIST 1.1 evaluation not described' may be also provided. Therefore, the user can immediately check the field from which input is omitted through the query, and input the missing data in the corresponding field by referring to the query and message to prevent data from not being entered.

In another embodiment, the query providing unit 30 automatically generates a query in a case in which the obtained image evaluation data does not conform to the evaluation rules, and stores and manages the generated query contents. That is, the query providing unit 30 tracks and documents a plurality of generated queries and provides them to the user. Based on the document in which the contents of the generated queries are organized, the user can check and correct the items that do not meet the evaluation rules at a glance.

The image evaluation data comparing and analyzing unit 40 checks whether the plurality of pieces of image evaluation data obtained from the plurality of evaluators match each evaluation item.

In an embodiment, the image evaluation data comparing and analyzing unit 40 compares and analyzes the plurality of pieces of image evaluation data to automatically provide mismatch evaluation items. Since the moderator can adjust and determine the automatically provided mismatch evaluation items without manually searching for the provided mismatch evaluation items, it is possible to make final judgment more conveniently and to generate final image evaluation data.

Figure 3:
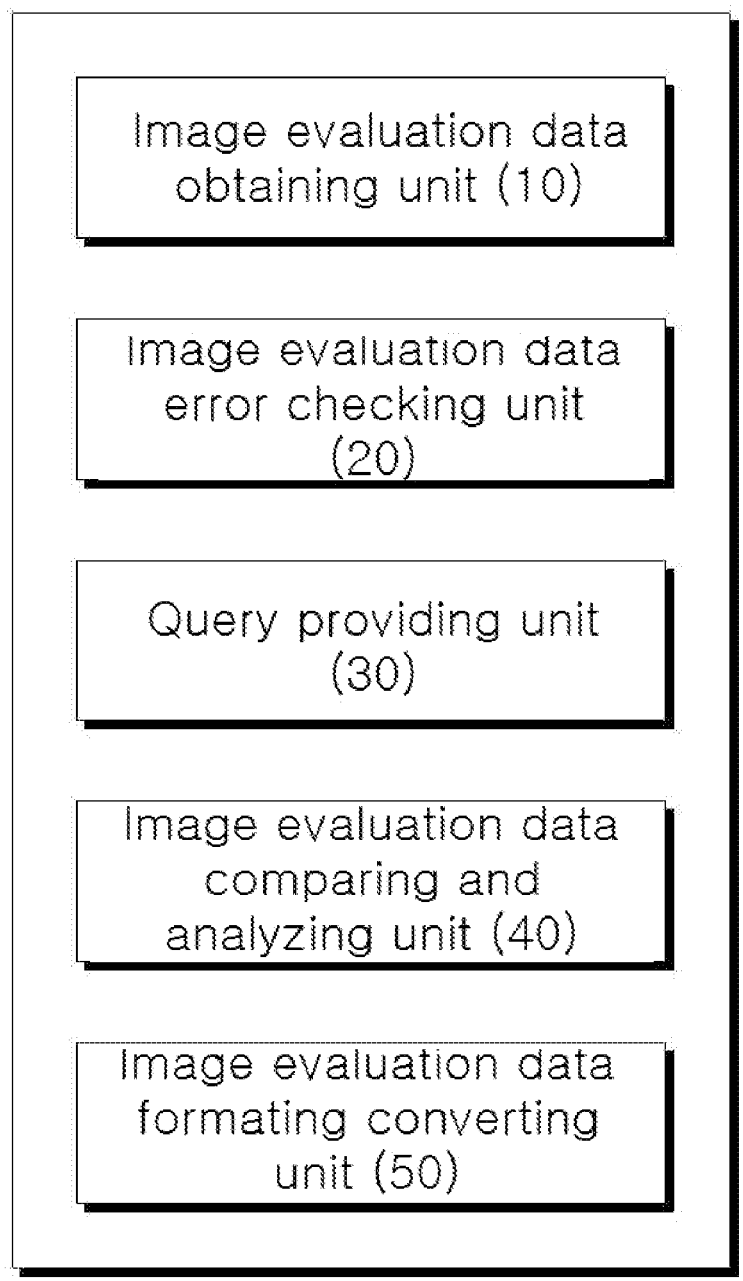
FIG. 3 is a diagram illustrating the system for automatically managing clinical trial image evaluation data including an image evaluation data error determining unit according to an embodiment of the present disclosure.

FIG. 3 is a diagram illustrating the system for automatically managing clinical trial image evaluation data including an image evaluation data error determining unit according to an embodiment of the present disclosure.

Referring to FIG. 3, the system 100 for automatically managing clinical trial image evaluation data according to an embodiment of the present disclosure further include an image evaluation data format converting unit 50.

The image evaluation data format converting unit 50 serves to convert the obtained final image evaluation data into a standard format.

"Standard format" is a reference data format. For example, the standard format may be a study data tabulation model (SDTM) format of CIDSC (clinical data interchange standards consortium), but is not limited thereto, and may be an arbitrary data format required in domestic and foreign countries.

The image evaluation data format converting unit 50 converts the final image evaluation data into an automatically set standard format. Therefore, the user can obtain image evaluation data made in the standard format more conveniently without needing to manually convert the data format.

On the other hand, in an embodiment, the image evaluation data format converting unit 50 can convert the image evaluation data not into the standard format but into various formats, e.g., csv, image, MS office, etc., as occasion demands.

Figure 4:
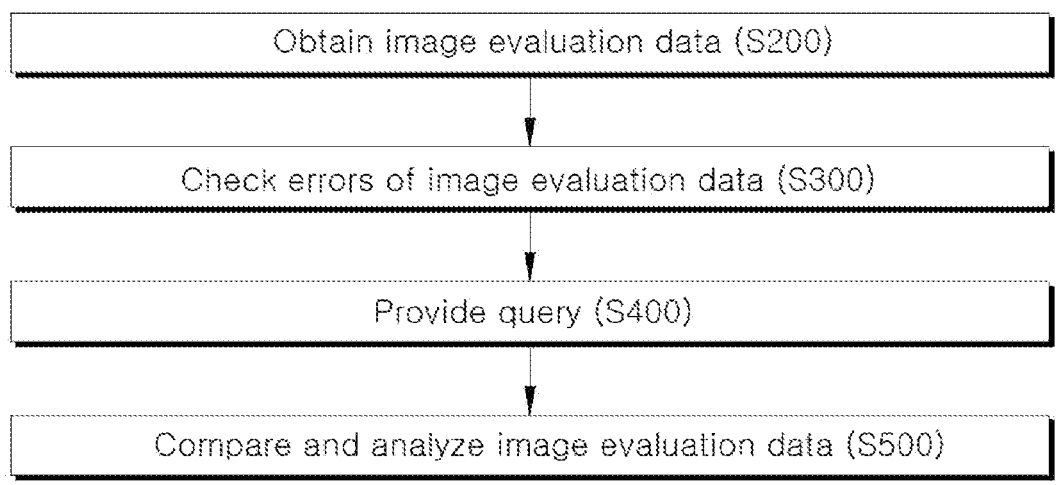
FIG. 4 is a flow chart schematically illustrating a method for automatically managing clinical trial image evaluation data according to an embodiment of the present disclosure.

FIG. 4 is a flow chart schematically illustrating a method for automatically managing clinical trial image evaluation data according to an embodiment of the present disclosure.

Referring to FIG. 4, the method for automatically managing clinical trial image evaluation data according to an embodiment of the present disclosure includes an image evaluation data obtaining operation (S200), an image evaluation data error determining operation (S300), a query providing operation (S400), and an image evaluation data comparing and analyzing operation (S500).

In operation S200, the image evaluation data obtaining unit 10 obtains image evaluation data from a plurality of image evaluators, respectively.

In an embodiment, the image evaluation data includes a numerical analysis value for a target object. Moreover, the numerical analysis value is calculated based on the reference data included in the evaluation rules. The "reference data" includes a measurement standard prepared for types of target objects (for example, in a case in which the target object is a tumor, the standard for measuring a diameter according to kinds of tumors). A detailed description thereof will be described later with reference to FIG. 5.

In operation S300, the image evaluation data error determining unit 20 analyzes whether the image evaluation data obtained through the image evaluation data obtaining unit 10 conforms to the preset evaluation rules for each evaluation item.

In operation S400, the query providing unit 30 automatically generates and provides a query for evaluation items that do not meet the evaluation rules based on the analysis result of the image evaluation data error inspection unit 20.

In an embodiment, the query providing unit 30 generates and provides a query in real-time even while the evaluator inputs the image evaluation data. That is, in operation S400, the evaluator refers to the automatically generated query to input image evaluation data more accurately without omission.

In another embodiment, after the evaluator finishes inputting the image evaluation data, the query providing unit 30 generates one or more queries based on the results of the error determining unit 20 determining the image evaluation data to provide them at a time. That is, each query can be generated and documented for each of the evaluation items that do not conform to the evaluation rules included in the entire obtained image evaluation data. Therefore, the evaluator can check and correct errors such as miswriting, typos, and omissions in the input image evaluation data.

In operation S500, the image evaluation data comparing and analyzing unit 40 automatically compares and analyzes the plurality of pieces of image evaluation data.

In an embodiment, the query providing unit 30 generates a query based on the result of the image evaluation data comparing and analyzing unit 40 comparing and analyzing the plurality of pieces of image evaluation data. That is, the operation S400 may be performed before or after the operation S500 step, or before and after the operation S500 step. In a case in which operation S400 is performed after step S500, the evaluator can improve the accuracy of evaluation by determining and evaluating items that do not match those of the image evaluation data input by other evaluators.

Figure 5:
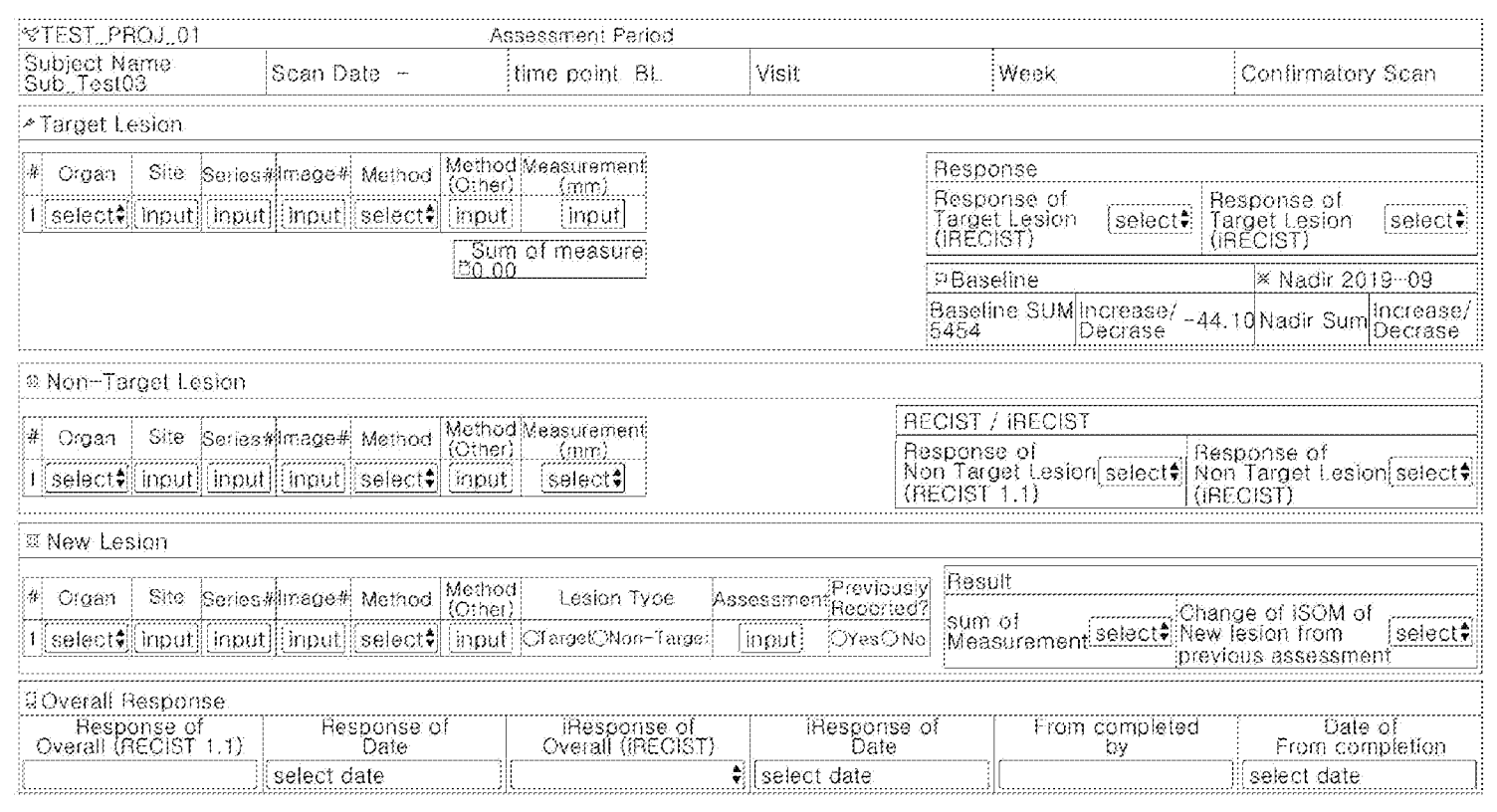

FIG. 5 is an exemplary diagram of a UI provided to an evaluator based on reference data according to an embodiment of the present disclosure.

For example, the reference data may be an evaluation criterion provided by response evaluation criteria in solid tumors (RECIST).

The system 100 makes data of evaluation criteria provided by the RECIST, stores and manages the data beforehand, and then, generates a query based on the data or automatically calculates a numerical analysis value 220 for reference.

For example, reference data includes response evaluation criteria in solid tumors (RECIST) specified in RECIST 1.1. Specifically, total five target lesions can be selected as target lesions from all affected organs based on size, and a maximum of two lesions can be selected within one organ site. In addition, the evaluation of the response to the target lesion is divided into CR, PR, PD, SD, and NE according to the following conditions.

TABLE 1

| | |
|---|---|
| Complete response(CR) | In a case in which shortening of All pathological lymph nodes is reduced to less than 10 mm |
| Partial response(PR) | In a case in which the sum of the diameters of the target lesions based on the sum of the baseline diameters decreases 30% or more |
| Disease progression(PD) | In a case in which the sum of the diameters of the target lesions based on the minimum sum during the trial increases 20% or more |
| Safe disease(SD) | In a case in which the decrease is insufficient to be the PR and the increase is insufficient to be the PD based on the minimum sum of the diameters during the trial |

Referring to FIG. 5, the system 100 provides a user interface (UI) configured to allow the evaluator to input image evaluation data according to the RECIST. That is, the system 100 provides a UI so that the evaluator can input image evaluation data to satisfy the reference data included in the evaluation rules. Furthermore, the system 100 generates and provides a query when the image evaluation data obtained from the evaluator does not match the reference data, so as to induce the evaluator to input image evaluation data matching the reference data by.

Figure 6A:
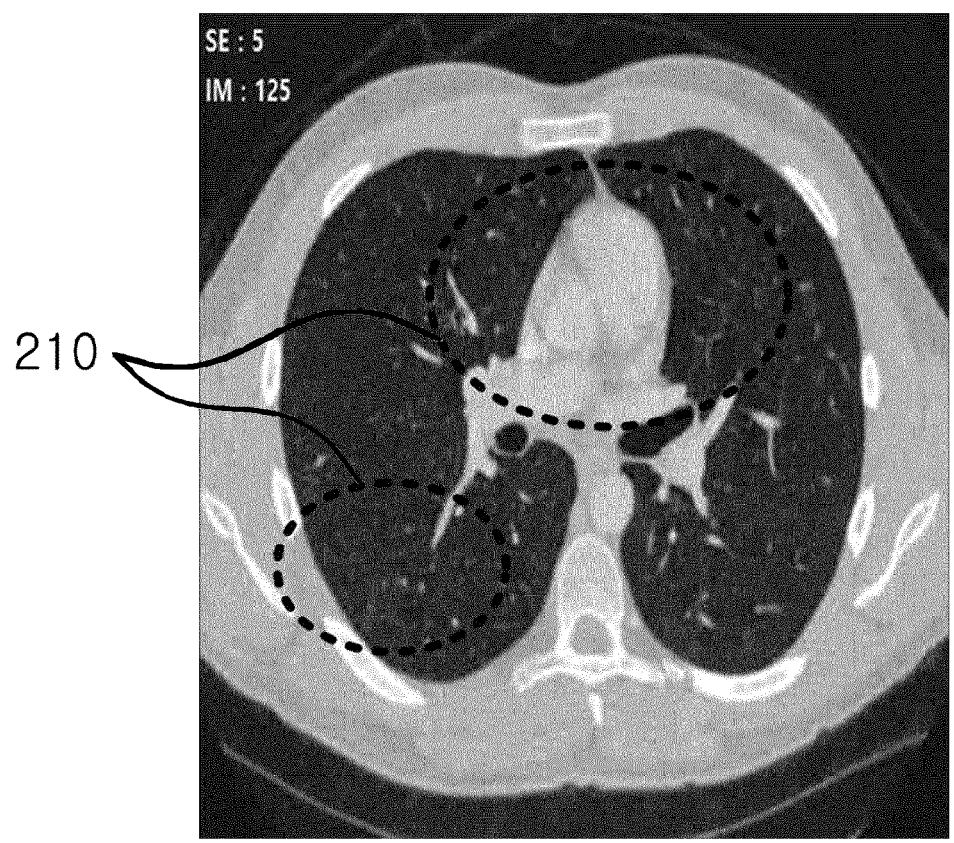
FIGS. 6A and 6B are exemplary diagrams illustrating a state in which a region of interest is set to obtain a numerical analysis value for reference according to an embodiment of the present disclosure.
Figure 6B:
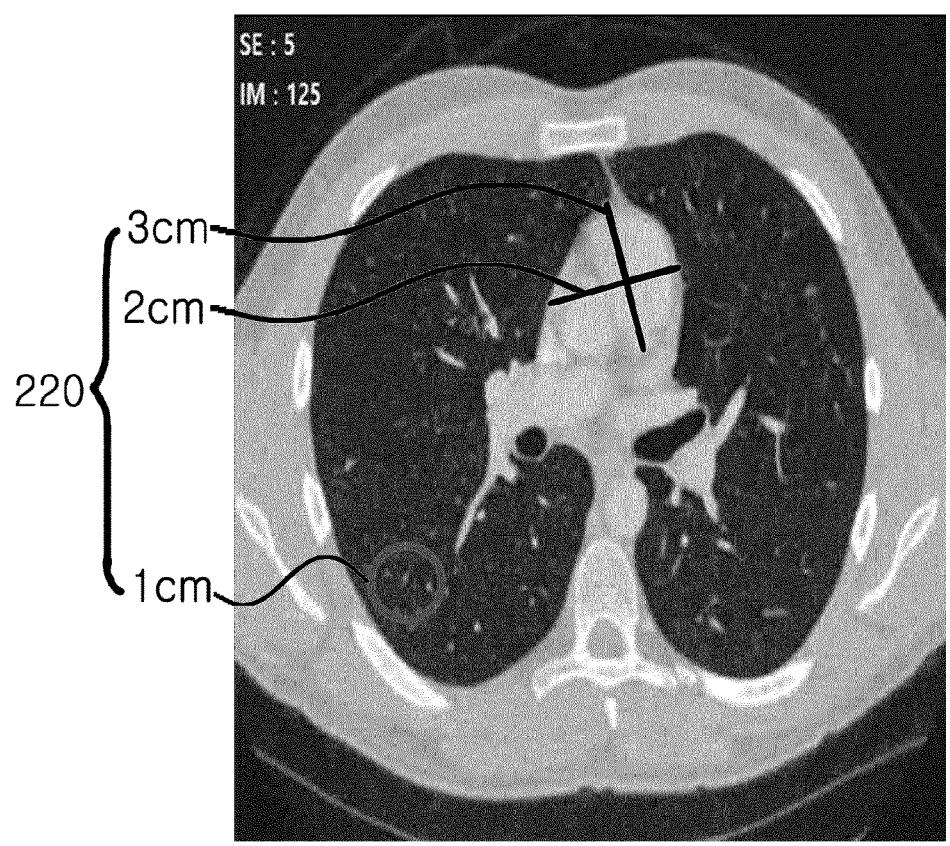

FIGS. 6A and 6B are exemplary diagrams illustrating a state in which a region of interest is set to obtain a numerical analysis value for reference according to an embodiment of the present disclosure.

"Numerical analysis value 220 for reference" is a numerical analysis value automatically measured and calculated by the system 100, and is a value provided so that the evaluator can refer to measuring a numerical analysis value included in the image evaluation data.

In an embodiment, the system 100 further includes a region of interest (ROI) setting unit (not shown) and a numerical analysis value measuring unit (not shown) for reference.

The region of interest setting unit serves to set a region of interest (ROI) in the clinical trial image. That is, the region of interest setting unit receives an approximate region with respect to a region estimated to have a target object from the evaluator, and sets the region as a region of interest 210.

The numerical analysis value measuring unit for reference automatically measures and provides the numerical analysis value 220 for reference with respect to the target object in the set ROI 210. That is, the numerical analysis value measuring unit for reference analyzes and provides the presence, number, size, etc. of target objects in the set region of interest 210.

FIG. 6A illustrates the setting of the region of interest 210, and FIG. 6B illustrates a state in which a numerical analysis value 220 for the target object within the set region of interest 210 is calculated.

In a case in which the evaluator roughly sets the region of interest 210 to include the region estimated to have the target object, the system 100 measures and calculates a numerical analysis value 220 for the target object in the region of interest based on the preset evaluation rules.

Specifically, referring to FIG. 6B, the target object in the form of a garden displayed at the bottom of the left side is provided by measuring its diameter according to the evaluation rules, and the target object displayed at the top is provided by measuring two diameters perpendicular to each other based on a specific point according to the evaluation criteria. As described above, because the numerical analysis value 220 for reference is automatically calculated and provided, the evaluator can reduce the error rate by comparing the automatically calculated numerical analysis value 220 for reference with the numerical analysis value measured by the evaluator.

In an embodiment, the numerical analysis value measuring unit for reference measures and calculates the numerical analysis value for reference based on basic information obtained from the evaluator. For example, basic information obtained from the evaluator includes a clinical trial imaging method (e.g., at least one among CT, MRI, PET/CT, and bone scanning), a target organ (e.g., at least one among the lung, liver, brain, etc.), a type of the target object (e.g., at least one among tumor, lymph node, cancer cell, etc.), and the like. The numerical analysis value measuring unit for reference measures and calculates a more accurate numerical analysis value for reference based on the above.

Meanwhile, in another embodiment, the numerical analysis value may be calculated based on the maximum diameter of the target object. For example, in a case in which the numerical analysis value is the length, the maximum diameter is calculated as a length value. Additionally, in a case in which the target object is circular or spherical, the area or volume is calculated by using the maximum diameter as the diameter.

FIG. 7 is an exemplary diagram illustrating a query provided to the evaluator in the process of obtaining image evaluation data according to an embodiment of the present disclosure.

Referring to FIG. 7, the query providing unit 30 provides a query by determining whether the image evaluation data input by the evaluator meets the evaluation rules for each evaluation item. Specifically, a query of 'please input value' is provided to an item having missing input, and a query of 'please input value bigger than 5 mm' is provided to an item exceeding the range. On the other hand, items input to conform to the evaluation rules are indicated by colors, symbols, or the likes to be distinguished from mismatch items.

Figure 8:
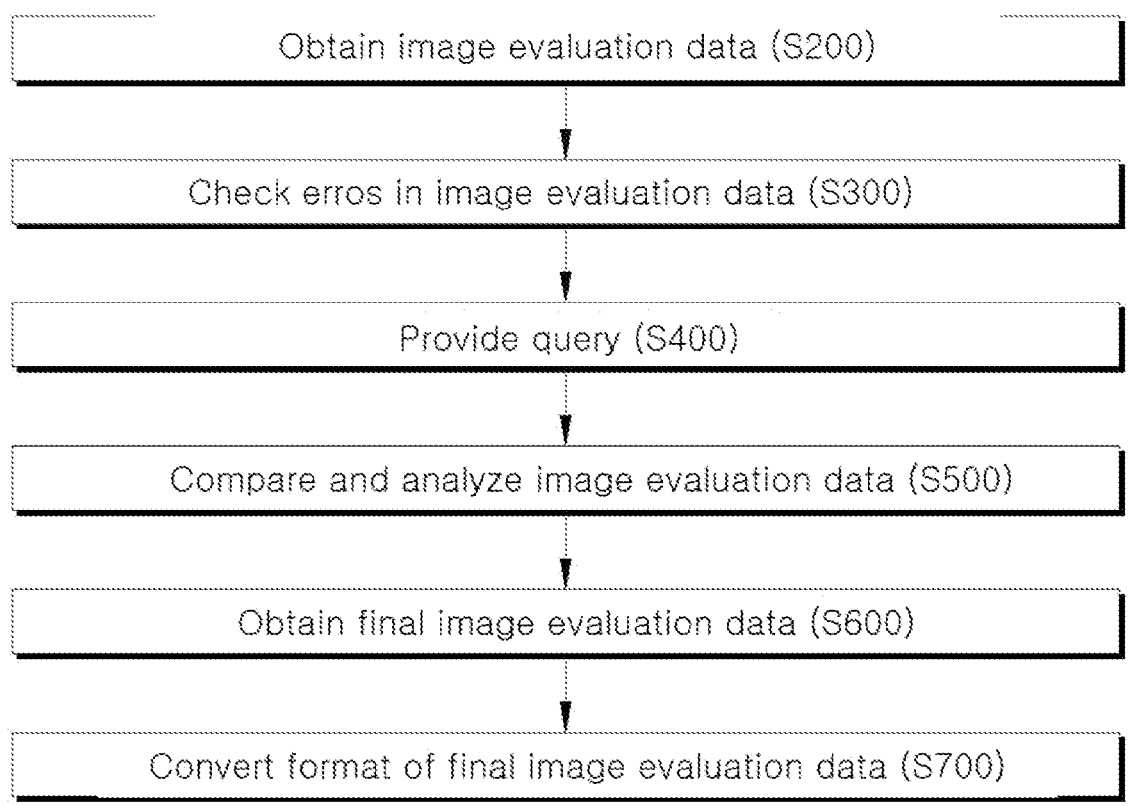
FIG. 8 is a flow chart schematically illustrating a method for automatically managing clinical trial image evaluation data including the operation of obtaining the final image evaluation data and converting the format of the final image evaluation data according to an embodiment of the present disclosure.

FIG. 8 is a flow chart schematically illustrating method for automatically managing clinical trial image evaluation data including the operation of obtaining the final image evaluation data and converting the format of the final image evaluation data according to an embodiment of the present disclosure.

Referring to FIG. 8, the method for automatically managing clinical trial image evaluation data according to an embodiment of the present disclosure further includes a final image evaluation data obtaining operation S600, and a final image evaluation data format converting operation S700.

Operation S600 is to obtain final image evaluation data from the moderator. The moderator performs adjustment based on the comparative analysis result of the plurality of pieces of image evaluation data performed by the system so as to generate the final image evaluation data.

Operation S700 is to automatically convert the final image evaluation data obtained in operation S600 into a standard format.

FIG. 9 is an exemplary diagram illustrating a state in which a mismatch evaluation item is provided according to an embodiment of the present disclosure.

The system 100 compares and analyzes the plurality of obtained image evaluation data, and provides mismatch evaluation items among the plurality of pieces of image evaluation data.

Referring to FIG. 9, it is confirmed that the first to third evaluators perform evaluation on the same clinical trial image and input image evaluation data, and the evaluation result (response) does not match.

Specifically, the first evaluator and the second evaluator evaluate SD (safe disease), and the third evaluator evaluated PD (disease progression). The system 100 automatically detects a mismatch item, and provides the detected mismatch item and a query, 'a response (iRECIST) value is mismatched. Please select a reading result.' To the moderator. Therefore, the moderator can check the automatically provided mismatch item without needing to search the mismatch item manually, and perform adjustment and determination through a final decision.

FIG. 10 is an exemplary diagram illustrating a state in which the image evaluation data is converted into SDTM format of CDISC according to an embodiment of the present disclosure.

As illustrated in FIG. 10, in a case in which there is a difference in standard format between the automatically obtained image evaluation data and the image evaluation data input by the evaluators and the moderators, the system 100 converts the automatically obtained image evaluation data into the standard format.

According to the present disclosure, since most of the clinical trial image evaluation procedures are performed not manually but automatically, it is possible to reduce reading by the evaluators, adjustment by the moderators, and management by a manager and to manage the clinical trial image evaluation data more rapidly and effectively.

Additionally, the system and method according to the present disclosure provide queries and help so that the evaluator can input image evaluation data while observing the evaluation criteria and procedures, thereby minimizing technical errors and obtaining and managing very effective image evaluation data.

In addition, the system and method according to the present disclosure can integrate and comprehensively manage the plurality of procedures for evaluating clinical trial images by just one system.

The method or algorithm described in relation to the embodiments of the present disclosure can be directly embodied in hardware, can be embodied in a software module executed by hardware, or can be embodied by combination thereof. The software module can reside in a random access memory (RAM), a read-only memory (ROM), an erasable programmable read-only memory (EPROM), an electrically erasable programmable read-only memory (EEPROM), a flash memory, a hard disk, a detachable disk, a CD-ROM, or a medium readable by a computer, well-known in the technical field to which the present disclosure belongs.

The above description is only exemplary, and it will be understood by those skilled in the art that the disclosure may be embodied in other concrete forms without changing the technological scope and essential features. Therefore, the above-described embodiments should be considered only as examples in all aspects and not for purposes of limitation.

The invention claimed is:

1. A method for automatically managing clinical trial image evaluation data, generated when a clinical trial image is evaluated, the method performed by a computer and comprising:
   obtaining first image evaluation data and second image evaluation data from a first evaluator and a second evaluator, respectively;
   analyzing the obtained image evaluation data by evaluation items, whether the obtained image evaluation data conforms to preset evaluation rules;
   in a case in which the obtained image evaluation data includes an evaluation item which does not conform to the evaluation rules, automatically providing a query including a correction request and help with respect to the evaluation item that does not conform to the evaluation rules;
   determining whether the first image evaluation data and the second image evaluation data match each other with respect to the evaluation items;
   obtaining final image evaluation data; and
   converting the final image evaluation data into a standard format,
   wherein the final image evaluation data is image evaluation data generated in a case in which a moderator performs adjustment based on image evaluation data input from a plurality of evaluators,
   wherein the image evaluation data include a numerical analysis value for a target object,
   wherein the numerical analysis value is calculated based on reference data included in the evaluation rules,
   wherein the reference data includes measurement standard for types of target objects, and
   wherein the obtaining comprises:
   setting a region of interest; and
   automatically measuring and providing the numerical analysis value for reference with respect to the target object in the region of interest.

2. The method of claim 1, wherein the numerical analysis value is at least one among a number, length, area, and volume of the target objects.

3. The method of claim 2, wherein the numerical analysis value is calculated based on the maximum diameter of the target object.

4. The method of claim 1, wherein in the determining, an evaluation item mismatched between the first image evaluation data and the second image evaluation data is provided.

5. The method of claim 1, wherein the standard format is a study data tabulation model (SDTM) format of clinical data interchange standards consortium (CIDSC).

6. A system for automatically managing clinical trial image evaluation data generated when a clinical trial image is evaluated, the system comprising:
   an image evaluation data obtaining unit which obtains first image evaluation data and second image evaluation data from a first evaluator and a second evaluator, respectively;
   an image evaluation data error determining unit analyzing the obtained image evaluation data by evaluation items, whether the obtained image evaluation data conforms to preset evaluation rules;
   a query providing unit automatically providing a query including a correction request and help with respect to an evaluation item that does not conform to the evaluation rules in a case in which the obtained image evaluation data includes the evaluation item which does not conform to the evaluation rules;
   an image evaluation data comparing and analyzing unit which checks whether the first image evaluation data and the second image evaluation data match each other with respect to the evaluation items; and
   an image evaluation data format converting unit which obtains final image evaluation data and converts the final image evaluation data into a standard format,
   wherein the final image evaluation data is an image evaluation data generated in a case in which a moderator performs adjustment based on image evaluation data input from a plurality of evaluators,
   wherein the image evaluation data includes a numerical analysis value for a target object,
   wherein the numerical analysis value is calculated based on reference data included in the evaluation rules,
   wherein the reference data includes measurement standard for types of target objects, and
   wherein the image evaluation data obtaining unit sets a region of interest and automatically measures and provides the numerical analysis value for reference with respect to the target object in the region of interest.

7. The system of claim 6, wherein the numerical analysis value is at least one among a number, length, area, and volume of the target objects.

8. The system of claim 7, wherein the numerical analysis value is calculated based on the maximum diameter of the target object.

9. The system of claim 6, wherein the image evaluation data comparing and analyzing unit provides a mismatch evaluation item between the first image evaluation data and the second image evaluation data.

10. The system of claim 6, wherein the standard format is a study data tabulation model (SDTM) format of clinical data interchange standards consortium (CIDSC).

\* \* \* \* \*